(12) United States Patent
Carlsen et al.

(10) Patent No.: US 8,617,320 B2
(45) Date of Patent: Dec. 31, 2013

(54) SYSTEM AND METHOD FOR CLEANING CONTAMINANT COLLECTION EQUIPMENT

(75) Inventors: Wayne D. Carlsen, Riverton, UT (US); Jared G. Maughan, Twin Falls, ID (US); Kris Nosack, Orem, UT (US); Joshem Coy Gibson, West Jordan, UT (US); Kelly Maureen Black, Twin Falls, ID (US); Jared V. Bradley, Cedar Hills, UT (US); Kevin Joseph Church, Twin Falls, ID (US)

(73) Assignee: Microbial-Vac Systems, Inc., Bluffdale, UT (US)

( * ) Notice: Subject to any disclaimer, the term of this patent is extended or adjusted under 35 U.S.C. 154(b) by 685 days.

(21) Appl. No.: 12/834,775

(22) Filed: Jul. 12, 2010

(65) Prior Publication Data
US 2011/0162675 A1 Jul. 7, 2011

Related U.S. Application Data

(60) Provisional application No. 61/224,831, filed on Jul. 10, 2009.

(51) Int. Cl.
| | |
|---|---|
| *B08B 9/032* | (2006.01) |
| *B08B 9/035* | (2006.01) |
| *B08B 3/04* | (2006.01) |
| *B08B 3/08* | (2006.01) |
| *B08B 3/10* | (2006.01) |

(52) U.S. Cl.
USPC .............. 134/166 C; 134/105; 134/166 R; 134/198

(58) Field of Classification Search
USPC ............ 134/104.1, 104.4, 166 C, 169 C
See application file for complete search history.

(56) References Cited

U.S. PATENT DOCUMENTS

| | | |
|---|---|---|
| 5,868,928 A | 2/1999 | Bradley |
| 6,550,347 B2 | 4/2003 | Bradley |
| 7,100,461 B2 | 9/2006 | Bradley et al. |
| 2005/0546506 | 3/2005 | Bradley |

(Continued)

FOREIGN PATENT DOCUMENTS

| | | |
|---|---|---|
| EP | 0993331 | 4/2000 |
| JP | 07-063660 | 3/1995 |

(Continued)

OTHER PUBLICATIONS

PCT Application PCT/US2010/041751; filing date Jul. 12, 2010; Wayne D. Carlsen; ISR mailed Apr. 29, 2011.

*Primary Examiner* — Michael Kornakov
*Assistant Examiner* — Natasha Campbell
(74) *Attorney, Agent, or Firm* — Thorpe North & Western LLP

(57) ABSTRACT

A wash system for cleaning the exposed surfaces of a contaminant collection device that includes a source of pressurized cleaning solution and a rinse appliance. The rinse appliance includes a first flow path that is adapted to direct the pressurized cleaning solution against a plurality of interior surfaces of a sampling head of the contaminant collection device and a vacuum tube that couples the sampling head to a collection chamber of the contaminant collection device. The rinse appliance may also include a second flow path that is adapted to direct the pressurized cleaning solution against a plurality of interior surfaces of the collection chamber and a separator filter installed therein. The rinse appliance further includes a dipping tank adapted to receive the cleaning solution after passing through one of the first and second flow paths.

24 Claims, 14 Drawing Sheets

(56) References Cited

U.S. PATENT DOCUMENTS

2005/0196316 A1* 9/2005 Kochevar .................. 422/33
2008/0029128 A1* 2/2008 Beijbom et al. ............ 134/22.1
2008/0166752 A1* 7/2008 Samadpour .................. 435/31

FOREIGN PATENT DOCUMENTS

| | | |
|---|---|---|
| JP | 09-043253 | 2/1997 |
| JP | 2002/136937 | 5/2002 |
| WO | WO 98/56484 | 12/1998 |

* cited by examiner

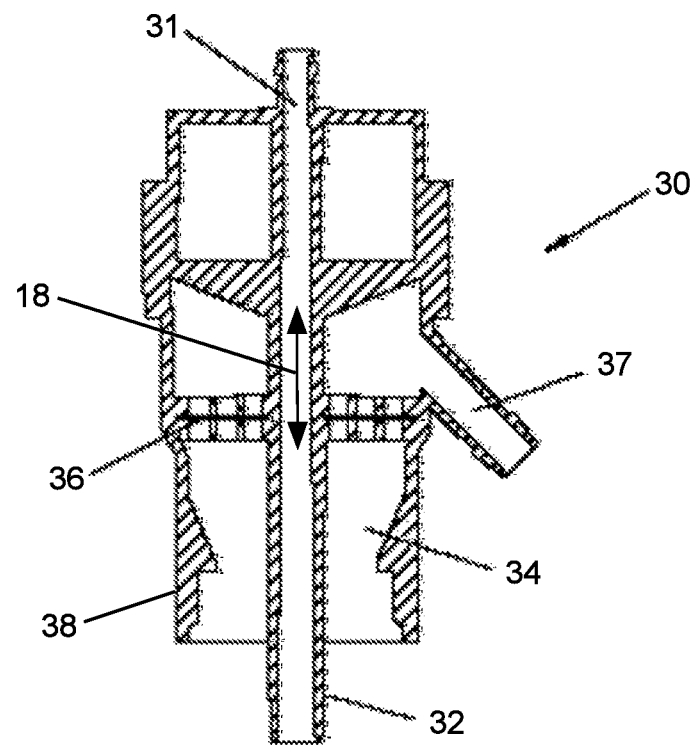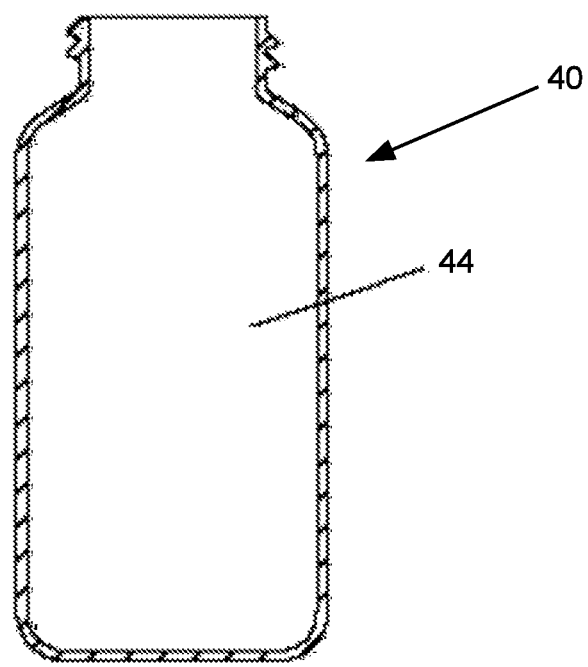
FIG. 2

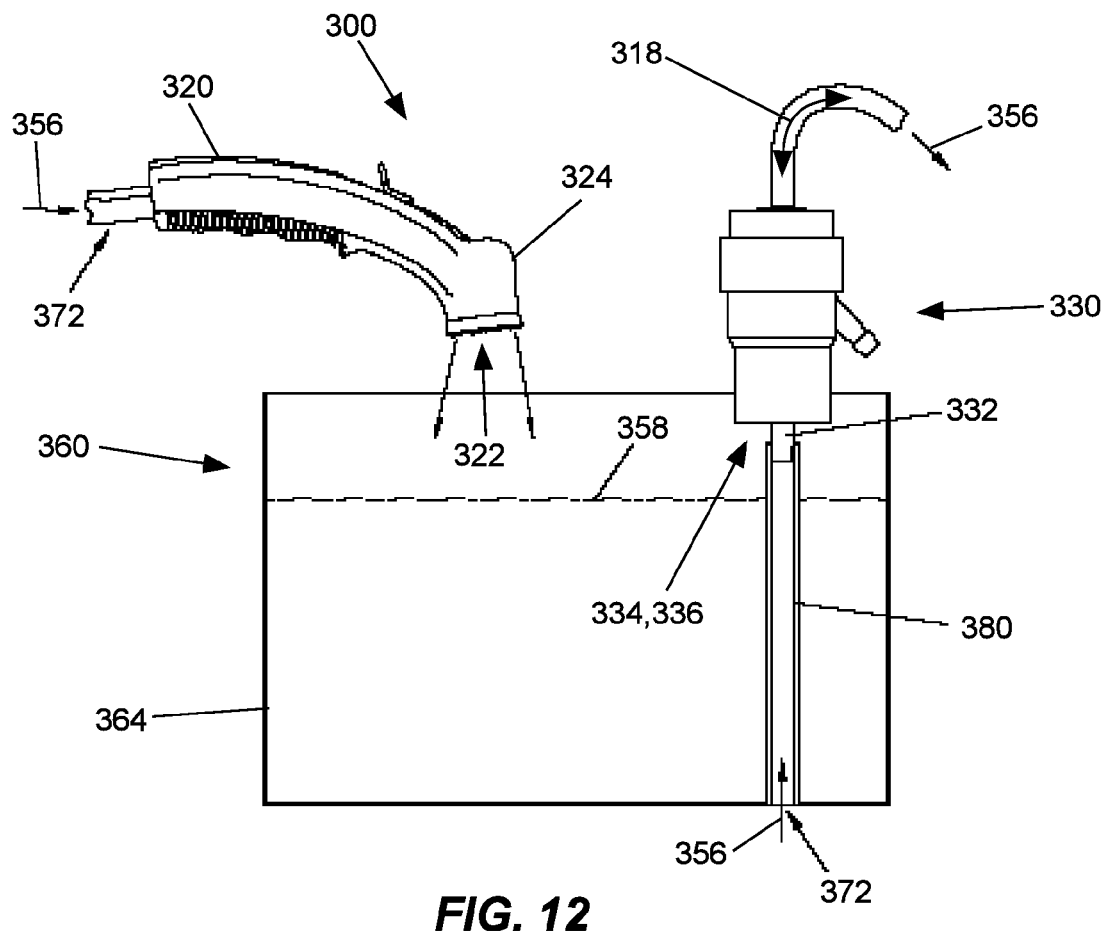
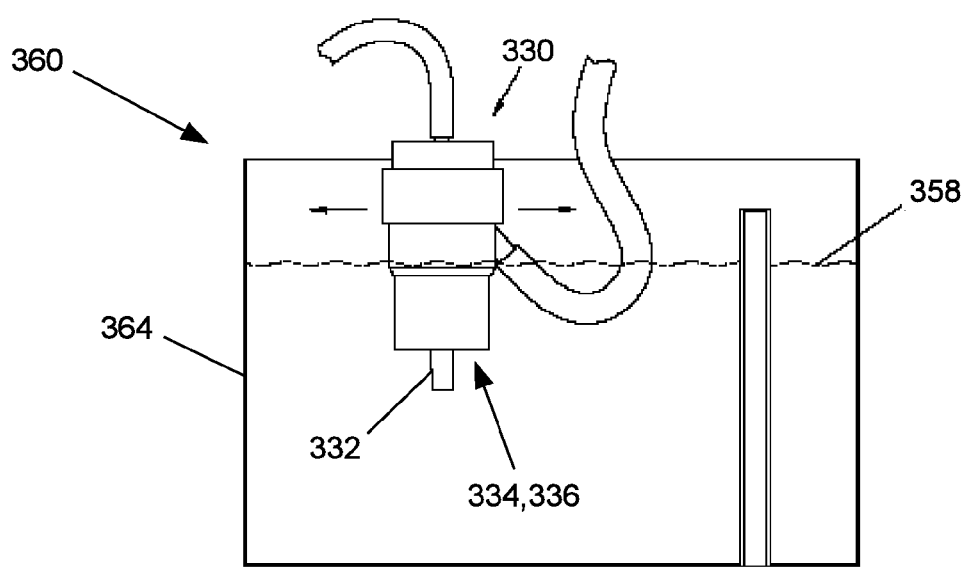

SYSTEM AND METHOD FOR CLEANING CONTAMINANT COLLECTION EQUIPMENT

RELATED APPLICATIONS

This application claims the benefit of U.S. Provisional Patent Application No. 61/224,831, filed Jul. 10, 2009, and entitled "System and Method for Cleaning Contaminant Collection Equipment," which application is incorporated by reference in its entirety herein.

FIELD OF THE INVENTION

The field of the invention relates generally to environmental samplers, and more particularly to portable field samplers for microorganisms, particulate contaminates and residues.

SUMMARY OF THE INVENTION

In accordance with one representative embodiment described herein, a wash system and method are provided for cleaning the components of a vacuum-type contaminant collection device which can be used to gather samples of microorganisms, particulate material and residues, etc. The various components of an exemplary collection device can include a sampling head, vacuum tubing, a separator with a separator filter, and a removable collection bottle, etc. The separator filter can be a hydrophobic filter.

In accordance with another representative embodiment described herein, a wash system having a source of pressurized cleaning solution and a rinse appliance is provided for cleaning the exposed surfaces of a contaminant collection device. The rinse appliance includes a first flow path that is adapted to direct the pressurized cleaning solution against a plurality of interior surfaces of a sampling head of the contaminant collection device and a vacuum tube that couples the sampling head to a collection chamber of the contaminant collection device. The rinse appliance may also include a second flow path that is adapted to direct the pressurized cleaning solution against a plurality of interior surfaces of the collection chamber and a separator filter installed therein. The rinse appliance further includes a dipping tank adapted to receive the cleaning solution after passing through the first flow path.

In accordance with another representative embodiment described herein, the rinse appliance includes a separator receptacle for receiving a separator of the contaminant collection device that includes a vacuum pathway rinse port that is centered within the separator receptacle and defining the first flow path, and which has a sealing surface located therein for receiving the separator's collection bottle stem. The separator receptacle also includes a rinse chamber surrounding the vacuum pathway rinse port and defining the second flow path, and having a collection chamber rinse nozzle formed therein for directing the cleaning solution against the collection bottle stem and the interior surfaces of the collection chamber and the separator filter. The separator receptacle can further include one or more drain openings in fluid communication with the rinse chamber that are adapted to drain the cleaning solution into the dipping tank.

In accordance with yet another representative embodiment described herein, the rinse appliance includes a debris removal surface positioned inside the dipping tank. The debris removal surface may either be submerged, partially submerged or simply in the dipping tank but above the water surface. The debris removal surface assists with the removal of debris from the sampling head during the cleaning process.

In a representative method, the cleaning fluid is caused to flow in a reverse direction (e.g. from the separator, through the vacuum tubing, and out of the sampling head). As the fluid exits the sampling head, the sampling head is rubbed against the debris removal surface so that the combination of the rubbing action and the flow of fluid removes any debris present in the sampling head. In situations where the debris removal surface is at least partially submerged, additional debris removal action is provided by the pool of cleaning solution.

In accordance with yet another representative embodiment described herein, a wash system is provided for cleaning the exposed surfaces of a contaminant collection device that includes a source of pressurized cleaning solution and a rinse appliance having a dipping tank, a sampling head receptacle and a separator receptacle. Moreover, the separator receptacle includes a vacuum pathway rinse port centered within a rinse chamber and with a first sealing surface located therein, and the rinse chamber surrounding the vacuum pathway rinse port and having a collection chamber rinse nozzle formed therein. The wash system can also include a sampling head of the contaminant collection device installed in the sampling head receptacle with a sampling head vacuum orifice supported above the dipping tank. The wash system can further include a separator of the contaminant collection device installed in the separator receptacle with a collection bottle stem sealing against the first sealing surface to establish communication with the vacuum pathway rinse port, and with a collection chamber surrounding the collection chamber rinse nozzle. Activation of a vacuum pathway rinse causes pressurized cleaning solution to flow along a first flow path against a plurality of interior surfaces of the sampling head and a vacuum tube that couples the sampling head to the interior of the collection bottle stem. Activation of a collection chamber rinse causes pressurized cleaning solution to flow along a second flow path against the collection bottle stem and a plurality of interior surfaces of the collection chamber and a separator filter installed therein.

In accordance with yet another representative embodiment described herein, the rinse appliance includes a dipping tank that is sub-divided into a primary dipping tank and one or more secondary dipping tanks. The primary dipping tank (or separator receptacle) includes a first flow path making connection with and directing rinse solution into the vacuum tubing and out through the sampling head. The primary dipping tank further includes a second flow path used to rinse and expose any of the exterior portions of the vacuum tubing extending down into the collection bottle as well as the interior surfaces of the separator and separator filter that form a portion of the collection chamber along with the collection bottle. Used cleaning solution exiting the separator can flow into the one or more secondary dipping tanks, which can also include a debris removal surface which can be used to clean the exterior surface of the sampling head proximate the vacuum orifice.

In accordance with yet another representative embodiment described herein, a rinse system is provided having a first flow path directing cleaning solution to the inside of the vacuum tubing and the sampling head, and a second flow path directing cleaning solution into a primary tank (or separator receptacle) that is sealed around the exterior of the collection chamber skirt to create a rinsing bath. The primary tank also includes a level- and pressure-setting snorkel or overflow tube. The snorkel or overflow tube generates a predetermined amount of hydrostatic pressure inside the rinsing bath that is sufficient to force any air remaining inside the primary tank to exit via the hydrophobic filter, thereby bringing all lower surfaces of the filter and filter support into contact with the cleaning solution.

In accordance with yet another representative embodiment described herein, a method is provided for cleaning the exposed surfaces of a contaminant collection device. The method includes the steps of obtaining a wash system comprising a pressurized source of cleaning solution and a rinse appliance having a separator receptacle and a dipping tank, and installing a separator of the contaminant collection device into the separator receptacle with the separator being coupled to a sampling head of the contaminant collection device with a vacuum tube. The method also includes the steps of directing a first flow of cleaning solution against a plurality of interior surfaces of the sampling head and the vacuum tube and out through a vacuum orifice of the sampling head in a direction opposite a direction of vacuum contaminant collection, and directing a second flow of cleaning solution against an outer surface of a collection bottle stem and the interior surfaces of the separator. The method further includes draining the second flow of cleaning solution into the dipping tank.

The method can also include the step of blowing air against a top surface of the separator filer in a direction opposite the direction of vacuum contaminant collection to remove any residual cleaning solution from the separator filter

BRIEF DESCRIPTION OF THE DRAWINGS

Features and advantages of the present invention will be apparent from the detailed description that follows, and when taken in conjunction with the accompanying drawings together illustrate, by way of example, features of the invention. It will be readily appreciated that these drawings merely depict representative embodiments of the present invention and are not to be considered limiting of its scope, and that the components of the invention, as generally described and illustrated in the figures herein, could be arranged and designed in a variety of different configurations. Nonetheless, the present invention will be described and explained with additional specificity and detail through the use of the accompanying drawings, in which:

FIG. 2 is a cross-sectional side view of the separator and collection bottle of the contaminant collection device of FIG. 1;

FIG. 12 is a schematic side view of a wash system for cleaning a contaminant collection device, in accordance with another representative embodiment;

FIG. 13 is a schematic side view of the wash system of FIG. 12;

DETAILED DESCRIPTION OF EXEMPLARY EMBODIMENTS

Figure 1:
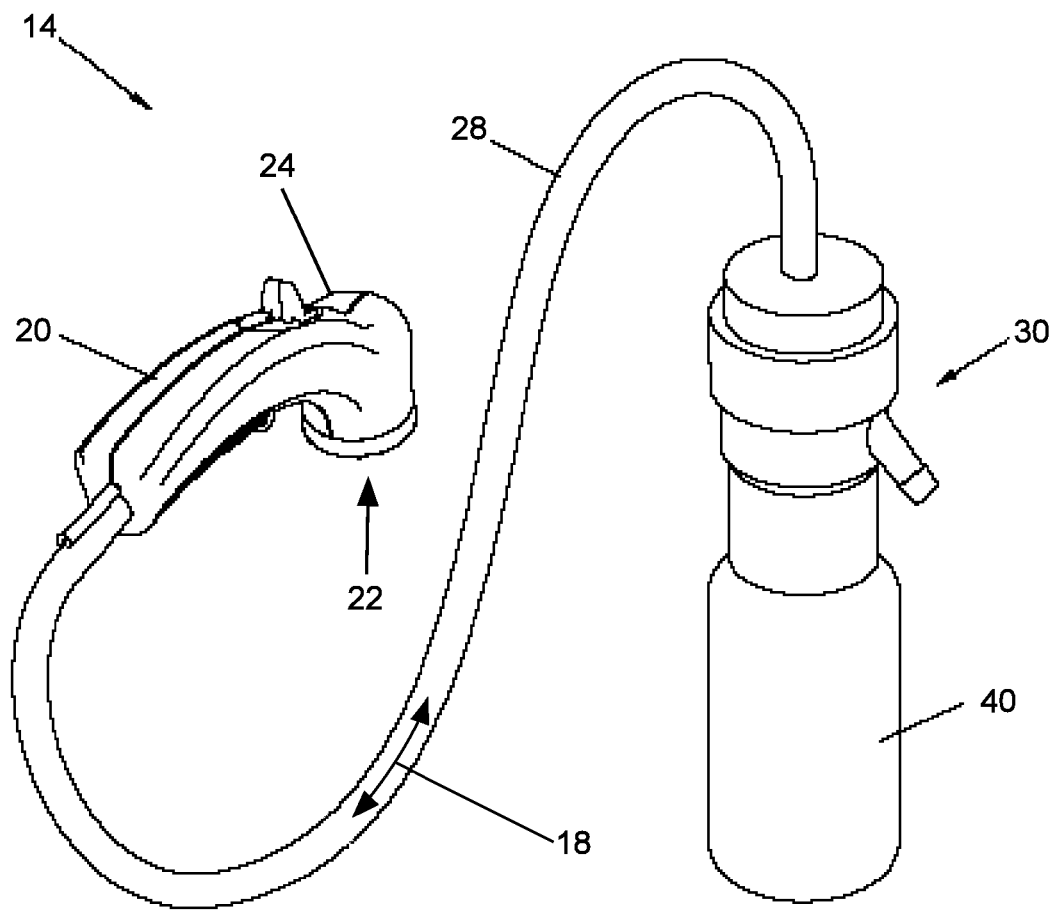
FIG. 1 illustrates a representative contaminant collection device of the type which can be cleaned with the wash system described herein.

The following detailed description makes reference to the accompanying drawings, which form a part thereof and in which are shown, by way of illustration, various representative embodiments in which the invention can be practiced. While these embodiments are described in sufficient detail to enable those skilled in the art to practice the invention, it should be understood that other embodiments can be realized and that various changes can be made without departing from the spirit and scope of the present invention. As such, the following detailed description is not intended to limit the scope of the invention as it is claimed, but rather is presented for purposes of illustration, to describe the features and characteristics of the representative embodiments, and to sufficiently enable one skilled in the art to practice the invention. Accordingly, the scope of the present invention is to be defined solely by the appended claims.

Furthermore, the following detailed description and representative embodiments of the invention will be best understood with reference to the accompanying drawings, wherein the elements and features of the embodiments are designated by numerals throughout.

DEFINITIONS

In describing and claiming the present invention, the following terminology will be used.

As used herein, "contaminant" refers to any foreign material or substance a user wishes to identify, sample or from which the user wishes to collect a specimen at a sample site, as well as any extra material or substances which may also be caught up in the sampling process, none of which the user would want to be carried over into a subsequent sample or specimen.

As used herein, "exposed surface" refers to one or more surfaces of a contaminant collection device, both internal and external, which may be come into contact with the contaminant material or substances being sampled during the sampling process.

The singular forms "a," "an," and "the" include plural references unless the context clearly dictates otherwise. Thus, for example, reference to "drain opening" includes reference to one or more of such structures, "cleaning solution"

includes reference to one or more of such fluids, and "directing" refers to one or more of such steps.

As used herein, the term "preferably" is also non-exclusive where it is intended to mean "preferably, but not limited to." Accordingly, the scope of the invention should be determined solely by the appended claims and their legal equivalents, rather than by the descriptions and examples given above.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, the term "about" is used to provide flexibility to a numerical range endpoint by providing that a given value may be "a little above" or "a little below" the endpoint.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually.

This same principle applies to ranges reciting only one numerical value as a minimum or a maximum. Furthermore, such an interpretation should apply regardless of the breadth of the range or the characteristics being described.

Embodiments of the Invention

Illustrated in FIGS. 3-18 are several representative embodiments of a wash system for cleaning contaminant collection equipment, such as the contaminant collection device shown and described with reference to FIGS. 1-2. The representative embodiments of the wash system also include one or more methods for cleaning the collection equipment.

As described herein, the wash system and method for cleaning the contaminant collection equipment can provide several significant advantages and benefits over other systems or methods for cleaning microorganism or particulate contaminate sampling devices. However, the recited advantages are not meant to be limiting in any way, as one skilled in the art will appreciate that other advantages may also be realized upon practicing the present invention.

The wash system and methods described herein may be used to clean one or more components of a contaminant collection device that employs a vacuum to gather samples of the microorganisms, particulate contaminants or liquid residues from various surfaces. For instance, in one exemplary sampling device the collected particulates, pathogens or bacteria, etc., can travel from the sampled surface to an enclosed collection chamber via a vacuum pathway that may include a sampling head, vacuum tubing, a separator and a collection bottle. The collection chamber may further include means for separating the air in the sample from the fluid and bacteria in the sample, such as a hydrophobic filter. The hydrophobic filter may reside in what would be deemed the top part of the collection chamber and secured with threads, a clamp or other means that can also be used to couple the collection bottle to the collection chamber located in a lower portion of the separator.

During collection suction can be applied to the opposite side of the hydrophobic filter to create a differential pressure across the filter that pulls air flow through the filter and creates a vacuum inside the collection bottle. This in turn pulls air flow through the vacuum tubing to create air flow and a vacuum at the sampling head. The collection equipment components may also include a method for dispensing a collection fluid onto the surface to further enable the collection and transport of the bacteria from the surface to the collection bottle.

The collection equipment components can be provided in a sterile condition, and may include a removable collection bottle. In configurations where the collection bottle is removable, some end users may wish to use the same collection equipment again with a new bottle to avoid the expense of replacing all of the collection equipment components. However, in a typical use of the collection equipment the end user is often trying to identify what pathogens or bacteria are on a target sample surface, in which case any carryover from the previous sample or cross-contamination to the new sample surface from the previously sampled surface would be considered unacceptable. Thus, a cleaning system and method for removing most or nearly all contaminants from the various components of the collection device, and which allows for the re-use of the same collection equipment to accurately gather a new sample, would be highly beneficial.

Examples of specific contaminant collection devices may be found in U.S. Pat. No. 5,868,928, filed Jun. 10, 1997 and entitled "Microbial Sampler and Concentrator, U.S. Pat. No. 6,550,347, filed Nov. 30, 2000 and entitled "Vacuum Air Component Sampler", U.S. Pat. No. 7,100,461, filed Sep. 5, 2006 and entitled "Portable contaminant sampling system", and U.S. Patent Application Publication No. 2005/0054506, filed Jul. 30, 2004 and entitled "Microbial concentration system", each of which is incorporated by reference in its entirety herein.

The components of a representative contaminant sampling or collection device 14 are shown in FIG. 1. Microorganisms (including bacteria and pathogens), particulate matter, liquid or film residue or other contaminant material can enter the collection device through a vacuum orifice 22 located in the head end 24 of a sampling head 20, and can travel from the vacuum orifice 22 to the collection bottle 40 via a vacuum pathway 18. As illustrated in FIG. 1, the vacuum pathway 18 can include the sampling head 20, vacuum tubing 28 and a collection bottle 40 which can be used to capture and hold the contaminant specimen. In one aspect the contaminant collection device may also dispense a sample solution onto the surface to assist in collection the microorganisms or other collection debris or material from the surface which can be sprayed onto the surface prior to or during the process of collecting the bacteria, pathogens or other collection debris or material from the surface. Consequently, the contaminant collection device 14 may further include a separator 30 or similar means or mechanism for separating the air from the sample solution, microorganisms or other collection debris or material making up the contaminant specimen.

A representative separator 30 with a removable collection bottle 40 is shown in more detail in FIG. 2. The separator 30 can include a separator inlet 31 and a separator outlet 37. When the collection bottle 40 is connected to the collection chamber skirt 38 of the separator 30 and vacuum is applied to the separator outlet 37, a differential pressure can be developed and flow through the separator inlet 31 established. It is this flow which can create a vacuum at the sampling head's vacuum orifice via the vacuum pathway 18 and draw sample solution, bacteria, pathogens or other collection debris or material into the interior volume 44 of the collection bottle 40. During the collection process, the air, sample solution, bacteria, pathogens or other collection debris or material can be mixed together and may splash or spray as they travel down through the inside of the collection bottle stem 32 to enter the collection chamber 34 and collection bottle 40. Droplets or spray may collect on the exposed outer surfaces of the collection bottle stem 32 and the exposed interior surfaces of the collection chamber 34 of the separator that is in fluid communication with the interior volume 44 of the collection bottle 40.

The separator may further include a separator filter 36 or similar means for preventing the sample solution, microorganisms or other collection debris or material from leaving the collection chamber 34 and the interior volume 44 of the collection bottle 40. In one aspect the separator filter 36 can be a hydrophobic filter made of a material, such as PTFE, which repels water while allowing the passage of gases. In another aspect the separator filter can be a membrane or disc have a plurality of tortuous paths formed therein that can also inhibit the passage of liquids and/or solids while allowing the free movement of gases through the filter. In yet another aspect (not shown) the separator filter can be a cyclonic filter which separates the stream of collected liquids and entrained solids from the gas stream through the application of centrifugal motion. Regardless of the configuration or specific mechanism for separation of the gases from the liquids and solids, the separator filter 36 can create a barrier to the sample solution, microorganisms, or other collection debris or material while allowing air to freely pass from the collection chamber 34 to the separator outlet 37. During the collection process droplets or spray of the sample solution, micro-organisms and other collection debris can collect on the bottom surface or walls of the separator filter 36, and can be removed during the subsequent cleaning process described herein.

Figure 3:
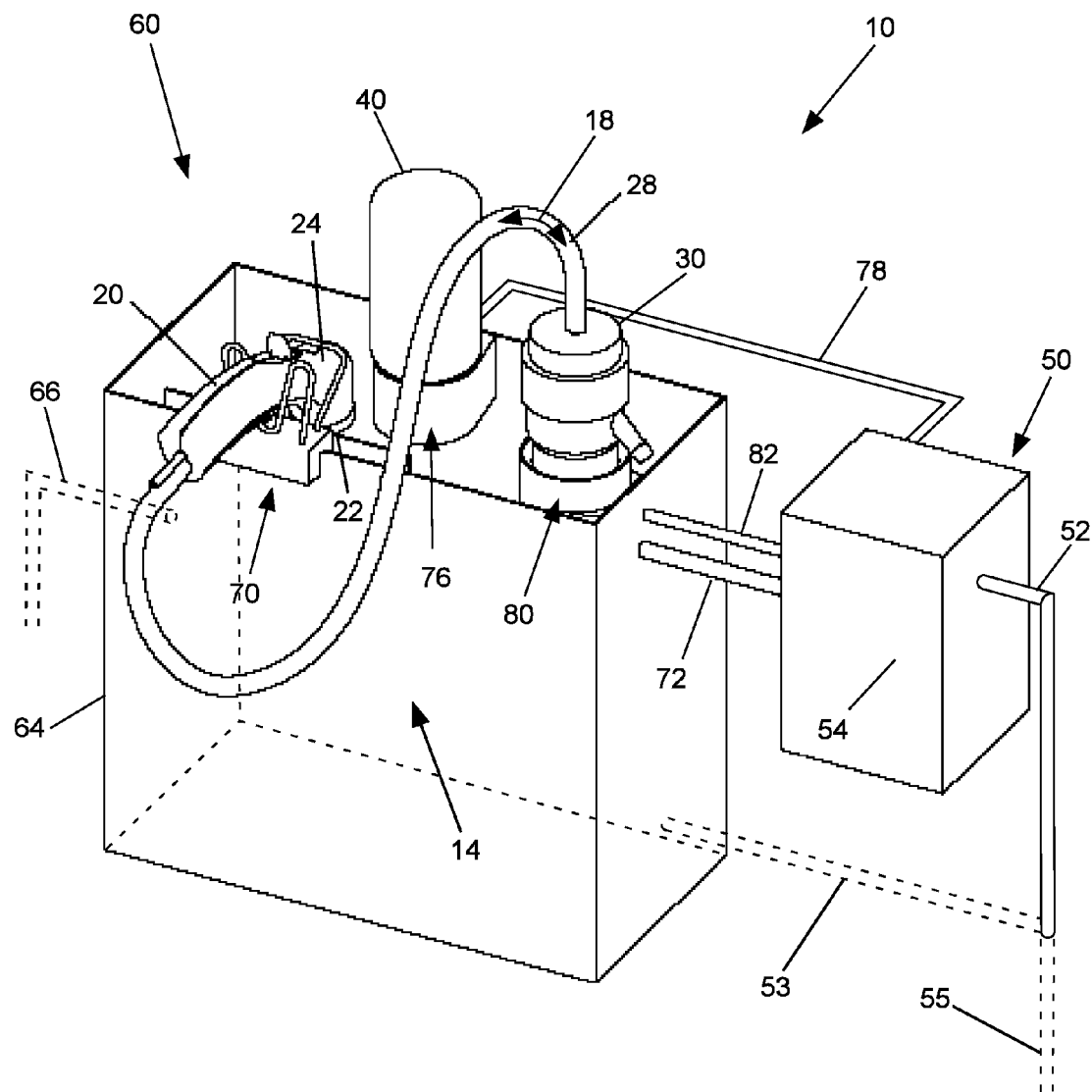
FIG. 3 is a perspective view of a wash system for cleaning a contaminant collection device, in accordance with one representative embodiment.

A representative cleaning or wash system 10 for removing or destroying microorganisms or other collection debris or material from the contaminant collection device 14 is shown in FIG. 3. The wash system 10 can include a source of pressurized cleaning solution 50 and a rinse appliance 60, which appliance can further include a dipping tank 64 and variety of holders or receptacles 70, 76, 80 for the various individual components of the contaminant collection device 14 illustrated in FIGS. 1-2. Moreover, each of the receptacles 76, 80 can also receive one or more streams of cleaning solution, including but not limited to a vacuum pathway rinse 72, a collection chamber rinse 82 and a collection bottle rinse 78, etc. The vacuum pathway rinse 72, for example, can comprise a flow of cleaning solution in a reverse direction (with respect to normal operation) through the vacuum pathway 18 that includes the collection bottle stem of the separator 30, the vacuum tubing 28 and the sampling head 20, and ultimately out the vacuum orifice 22 and into the dipping tank 64.

As further shown in FIG. 3, the source of pressurized cleaning solution 50 can include a supply line 52 of cleaning solution in fluid communication with a pressurization unit 54 which provides the one or more streams of pressurized cleaning solution 72, 82, 78 to the variety of holders or receptacles 70, 80, 76 suspended over the dipping tank. While the various flows can be split after discharge from a pressurization unit having a single pump, each of the individual streams may also be provided with its own dedicated pump to allow for the individual activation and control of each stream of pressurized cleaning fluid. Alternatively, it is to be appreciated that control valves (not shown) may also be placed in line in between the pressurization unit and the holders or receptacles in order to control or customize the flow and pressure of cleaning solution directed to each holder or receptacle when only a single pump is used.

In some wash system embodiments the cleaning solution can be re-circulated from the dipping tank 64 to the pressurization system 50 through a recycle line 53, while in other embodiments a supply of fresh cleaning solution 55 can be coupled to the supply line 52 as the used cleaning solution is drained away from the dipping tank 64 through drain outlet 66.

The rinse appliance 60 can include a sampling head holder or receptacle 70 that is configured to retain the sampling head 20 in a position such that the vacuum orifice 22 will drain into the dipping tank 64 when cleaning solution is flowing. Additionally, the head end 24 of the sampling head 20 may also be manually dipped or submerged into the cleaning solution contained within the dipping tank 64 during the cleaning process, as it can be especially advantageous to rinse the external portions of the sampling head 20 that surround the vacuum orifice 22 and which can also come into direct contact with the media being sampled by the contaminant collection device.

Figure 4:
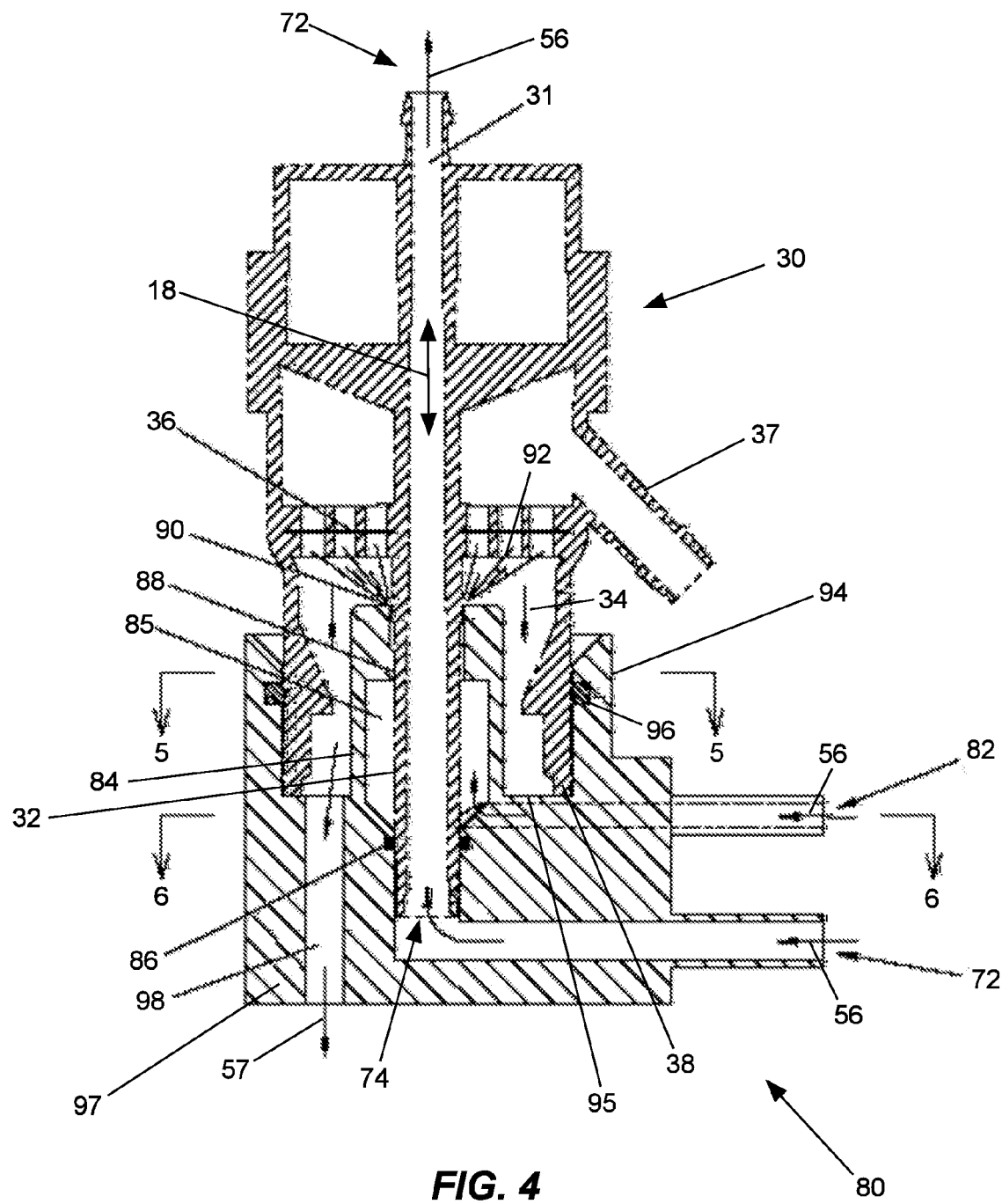
FIG. 4 is a cross-sectional side view of the separator and separator receptacle of the wash system of FIG. 3.

Referring now to FIG. 4, the rinse appliance can also include a separator receptacle 80 configured to apply two streams of cleaning solution 56 to the exposed surfaces of the separator 30 of the contaminant collection device. The first stream can be a vacuum pathway rinse 72 and the second stream can be a collection chamber rinse 82. The vacuum pathway rinse 72, for instance, can be used to apply cleaning solution in a reverse direction to the inside surfaces of the collection bottle stem 32 as the solution passes upwards towards the separator inlet 31 from a vacuum pathway rinse port 74 that is centered within the cup-shaped rinse chamber 94 of the separator receptacle 80. The cleaning solution can then continue past the separator inlet 31, through the vacuum tubing 28 and sampling head 20, and eventually exit the vacuum pathway 18 through the vacuum orifice 22 in the sampling head 20 (see FIG. 3).

Also shown in FIG. 4, the collection chamber rinse 82 can be used to apply the cleaning solution 56 to the outer surfaces of the collection bottle stem 32 as the liquid mixes and flows up through a solution pressure equalization chamber 85, which chamber can be located between the collection bottle stem 32 and inner surfaces of a nozzle stub 84 that projects upwardly from the bottom 95 of the separator receptacle's rinse chamber 94. The solution pressure equalization chamber 85 can be formed during insertion of the lower tip of the collection bottle stem 32 into a stem seal 86 situated within the vacuum pathway rinse port 74 when the separator 30 is removably installed into the separator receptacle 80.

From the solution pressure equalization chamber 85 the cleaning solution can continue to flow upward and out through a collection chamber rinse nozzle 90 with sufficient pressure to form a collection chamber rinse spray 92. The rinse spray 92 can scour and clean the remainder of the collection bottle stem 32, the bottom surfaces of the separator filter 36 and the interior surfaces of the collection chamber 34, all of which may be exposed to contaminants during the sampling process. An optimal distance between the collection chamber rinse nozzle 90 and the inner surfaces of the collection chamber 34 and separator filter 36 can be established when the bottom edge of the collection chamber skirt 38 comes into contact with the bottom surface 95 of the rinse chamber 94. During cleaning the collection chamber rinse spray 92 can flow down from these various surfaces to exit the rinse chamber 94 through one or more drains 98 formed through the base 97 of the separator receptacle 80.

During application of the collection chamber rinse 82, the collection chamber skirt 38 can be held in place within the rinse chamber 94 with an annular retention seal 96. The retention seal 96 can provide sufficient retentive force to prevent the separator 30 from inadvertently coming out of the rinse chamber 94 when the cleaning solution is flowing, while still maintaining a low enough retentive force to allow the end user to easily install and remove the separator 30 from the separator receptacle 80. The retention seal 96 can also substantially enclose the rinse chamber 94 so that the used cleaning solution 57 exits the chamber through the one or more drains 98 and not from any open gap between the collection chamber skirt 38 and the walls of the rinse chamber 94.

Figure 5:
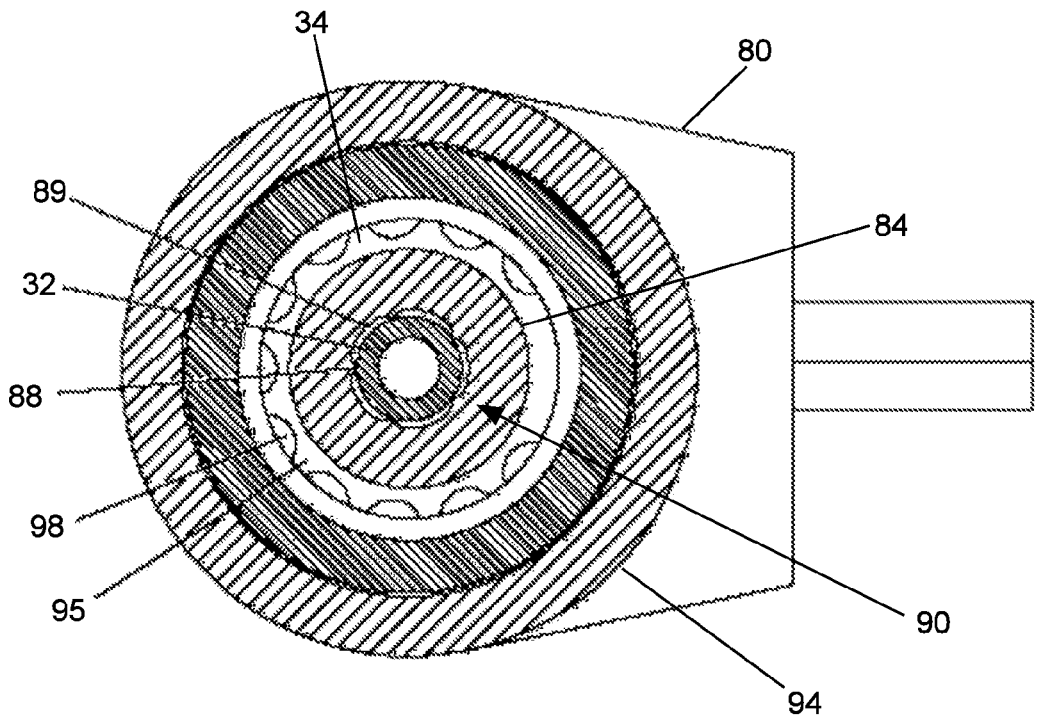
FIG. 5 is a cross-sectional top view of the separator and separator receptacle, as taken along Section Line 5-5 of FIG. 4.

Referring now to FIG. 5, in one aspect the nozzle stub 84 projecting upwardly from the center of the separator receptacle 80 can include centering ribs 88 located below the nozzle opening of the collection chamber rinse nozzle 90. The centering ribs 88 can operate to center the collection bottle stem 32 and create equal rinse nozzle gaps 89. Moreover, the centering ribs 88 can reside far enough below the nozzle opening 90 to allow the cleaning solution to become a cylindrical flow surrounding the circumference of the collection bottle stem 32 prior to exiting the nozzle 90 and entering the collection chamber, in order to provide a more uniform spray pattern. Also shown in FIG. 5 are the drains 98 openings through the bottom 95 of the rinse chamber 94.

Figure 6:
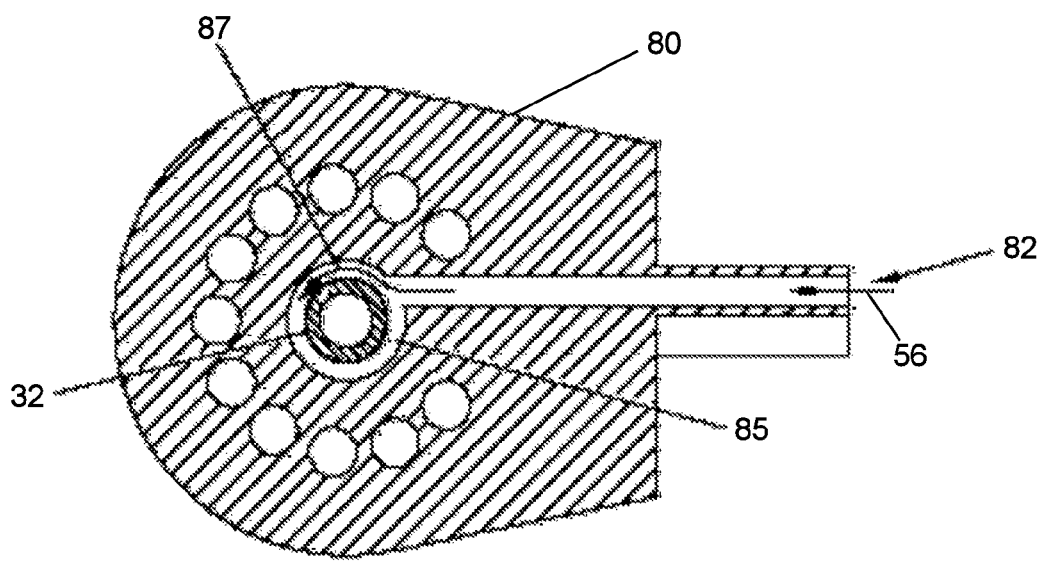
FIG. 6 is a cross-sectional top view of the separator and separator receptacle, as taken along Section Line 6-6 of FIG. 4.

In another aspect of separator receptacle 80 shown in FIG. 6, the collection chamber rinse 82 can enter the solution pressure equalization chamber 85 off center from the collection bottle stem 32 and create a vortex flow 87 in the solution pressure equalization chamber 85. The vortex flow 87 can equalize the pressures of the cleaning solution as it travels upward from the bottom of the solution pressure equalization chamber 85 near the stem seal 86 to the collection chamber rinse nozzle 90 while evenly distributing the cleaning force across the collection bottle stem 32.

Figure 7:
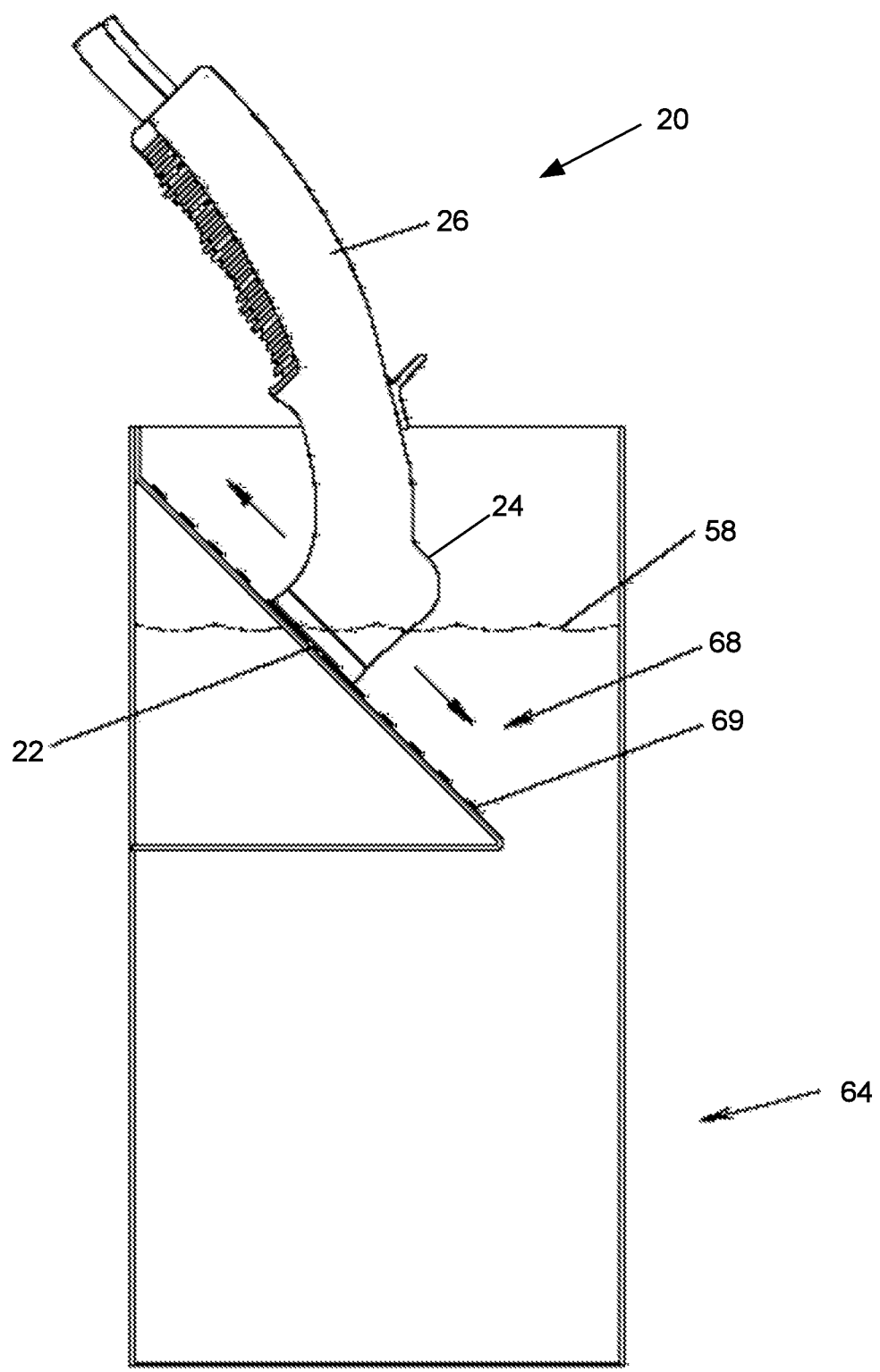
FIG. 7 is a schematic view of the sampling head and debris removal surface of the wash system of FIG. 3.

As illustrated in FIG. 7, the dipping tank 64 of the rinse appliance can include a debris removal surface 68. It is to be appreciated that the vacuum orifice 22 of the sampling head 20 can be configured to limit the size of debris that can enter the vacuum pathway 18. Due to this limitation and the adhesion forces of certain materials, debris may collect in and/or around the sampling head's vacuum orifice 22. To maintain the performance and cleanliness of the contaminant collection device the debris removal surface 68 can be used to remove the debris from around vacuum orifice 22 and head end 24 of the sampling head 20. This can be done by holding on to the handle grip 26 of the sampling head 20 and touching or pressing the flat portion of the head end 24 proximate to the vacuum orifice 22 against the debris removal surface 68 while moving it back and forth against the debris removal surface. This action may be done with cleaning solution flowing through the vacuum pathway 18 and out of the vacuum orifice 22. This action may also be done in the dipping tank 64, as shown in FIG. 7. The rubbing action may be done with the debris removal surface 68 above or below the surface of the cleaning solution 58. Furthermore, the debris removal surface 68 may have a number of surface features 69 to assist in the removal of the debris. The surface features 69 may include various treatments or texture designs. A nonexclusive representation of the surface features 69 would include a pattern of holes, indentations, bumps, overlays or tactile surface treatments, etc.

In another aspect of the washing system's rinse appliance, the dipping tank 64 can provide for the mechanical agitation of the debris removal surface itself and/or agitation of the pool of cleaning solution 58 located in the dipping tank 64 and proximate to the debris removal surface. In some aspects, such mechanical agitation can include application of ultrasonic vibrations or "sonication" of the debris removal surface, the cleaning solution, or both, to provide enhanced debris removal capabilities.

Figure 8:
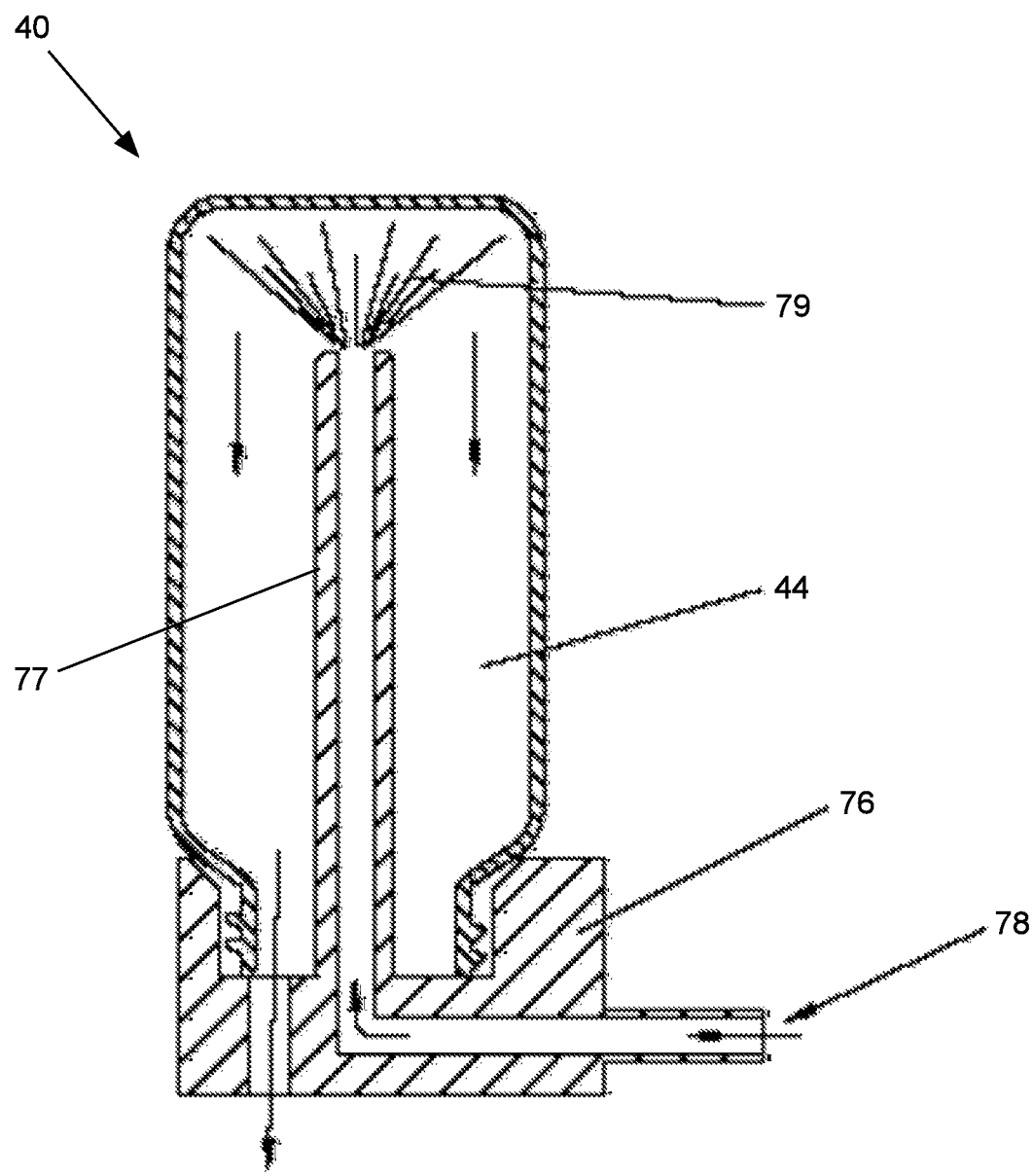
FIG. 8 is a cross-sectional side view of the collection bottle and collection bottle receptacle of the wash system of FIG. 3.

A cross-sectional side view of the collection bottle 40 and collection bottle receptacle 76 is provided in FIG. 8. After de-coupling from the separator, the collection bottle 40 can be inverted and installed over a collection bottle spout 77 projecting upward from the center of the collection bottle receptacle 76. The collection bottle rinse 78 can then be activated and directed through the spout 77 to produce a spray 79 of cleansing solution that cleans the interior surfaces of the collection bottle as the liquid runs down the inside of the collection bottle and out through one or more drains formed into the base of the collection bottle receptacle 76.

Figure 9:
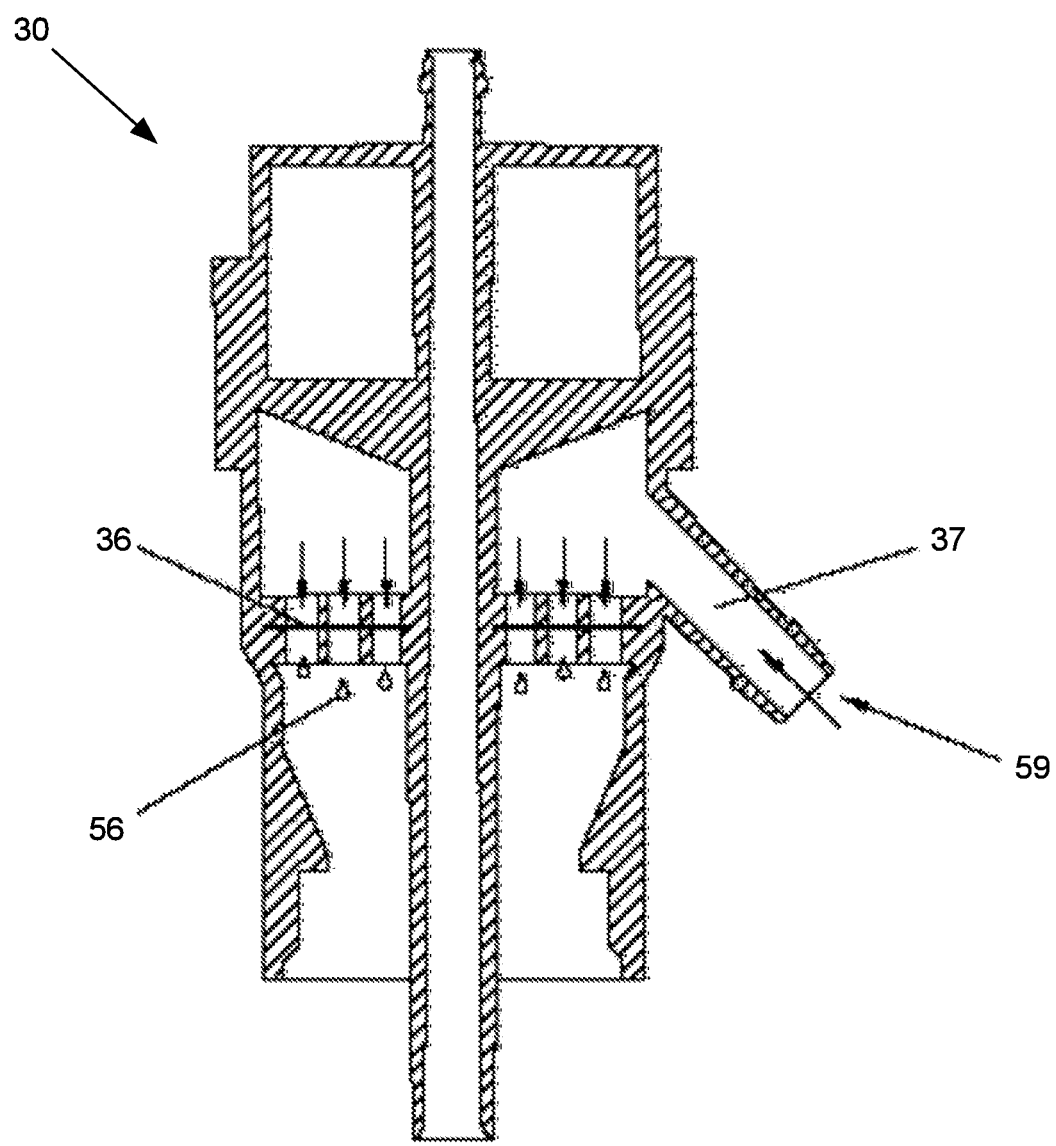
FIG. 9 is a cross-sectional side view of the separator of the wash system of FIG. 3

Illustrated in FIG. 9 is a representation of a regeneration step or process for the separator filter 36 which can take place after the first washing steps in the cleaning process are complete, after the separator has been removed from the separator receptacle, or after the collection chamber rinse has been deactivated etc. The cleaning system may include a reverse air flow mechanism 59 which pressurizes the separator outlet 37 and forces air through the separator filter 36 in the reverse direction, in the form of an instantaneous puff and/or a continuous flow. The puff or flow of reverse air can blow any residual liquids or droplets or cleaning solution 56 off from the bottom surface of the separator filter 36. The cleaning solution 56 may also include dead bacteria, dead pathogens or other collection debris or material that had been collected and splashed onto the separator filter 36.

Referring back to FIGS. 1-4 and 7, in one method of using the wash system 10 having a rinse appliance 60 with at least a separator receptacle 80, a debris removal surface 68 and a sampling head holder 70, the cleaning solution 56 can continuously flow through the vacuum pathway rinse 72 prior to installation of the separator 30 into the separator receptacle 80 to ensure that the separator receptacle 80 remains at the desired temperature and free from contaminants. When the end user desires to clean the contaminant collection device 14, they can insert the collection bottle stem 32 of the separator 30 into nozzle stub 84 of the rinse chamber 94 and continue directing the separator downwards until the lower skirt 38 of the collection chamber 34 contacts the bottom 95 of the rinse chamber 94 and the lower end of the collection bottle stem 32 seats against the stem seal 86 located in the vacuum pathway rinse port 74. During this downward motion the collection chamber rinse 82 can be activated so that the cleaning solution can immediately begin to the clean the surfaces of the collection bottle stem 32 and the collection chamber 34, and can continue to clean the interior surfaces of the vacuum pathway 18 as well as the interior surface of the collection chamber 34 and the outer surfaces of the collection chamber stem 32 which were exposed during the sampling process for a period of time after the separator was seated in the receptacle.

During this period of time the end user can also manipulate the sampling head 20 and rub the head end 24 against the debris removal surface 68 and remove debris and sampled material from around the vacuum orifice 22. The user can further dip the head end 24 of the sampling head 20 into the cleaning solution 58 in the dipping tank 64 to clean the areas near the vacuum orifice 22. If desired, in one aspect the gloved hands of the end user may also be dipped into the cleaning solution to further clean and sterilize the area around the contaminant collection device and reduce the risk of contaminant transfer between sampling sites. After cleaning in the dipping tank 64 the end user can then place the sampling head 20 in the sampling head holder 70 and wait for the remainder of the specified exposure time to pass, and until the cleaning cycle is complete.

The specified exposure time can depend on the type of cleaning solution. In one exemplary embodiment, for instance, the cleaning solution can be hot water that has been heated to a temperature ranging from about 160 degrees Fahrenheit to about 180 degrees Fahrenheit. It has been determined by the inventors of the wash system that direct contact with the heated water can result in a "thermal kill" of a majority, if not all, of the microorganisms present in the collection equipment within a few seconds, while a secondary heating of each individual component of the collection system 14 by the hot water can kill any remaining pathogens or bacteria not coming into direct contact with the cleaning solution within a slightly longer period of exposure time. It has been further determined that greater than 99% of the residual micro-organisms (such as pathogens and bacteria) can be destroyed by flowing a hot water cleaning solution for the specified exposure time, which can be up to about two minutes based on the microorganism of interest, but which can preferably be about one minute or less, and in one representative embodiment can be about thirty seconds or less. Similar results can be achieved using hot water heated to lower temperatures, up to about 140 degrees Fahrenheit, when the specified exposure time is increased to a period of three minutes or more. Positive results can also be achieved in shorter exposure times with cleaning solution that has been heated to about 200 degrees Fahrenheit or greater, up to and including the boiling point of water to produced pressurized steam which can then be directed into the various flow paths.

Other cleaning solutions or vapors can be used in representative cleaning systems described herein, and which can be utilized in representative methods which require only a single stage of cleaning (such as the hot water embodiment described above) or multiple cleaning stages that employ an active sanitizing solution stage followed by one or more rinsing or neutralizing stages. Illustrated in Table 1 is a non-exhaustive list of sanitizing solutions and neutralizing agents which can be used with various embodiments of the cleaning system of the present invention. Other cleaning solutions and neutralizing agents not included on the list but which can be employable with the representative cleaning systems described herein, for removing, rendering ineffective or destroying bacteria, pathogens or other microorganisms or contaminants remaining inside the collection equipment, shall be considered to fall within the scope of the present invention.

Figure 10:
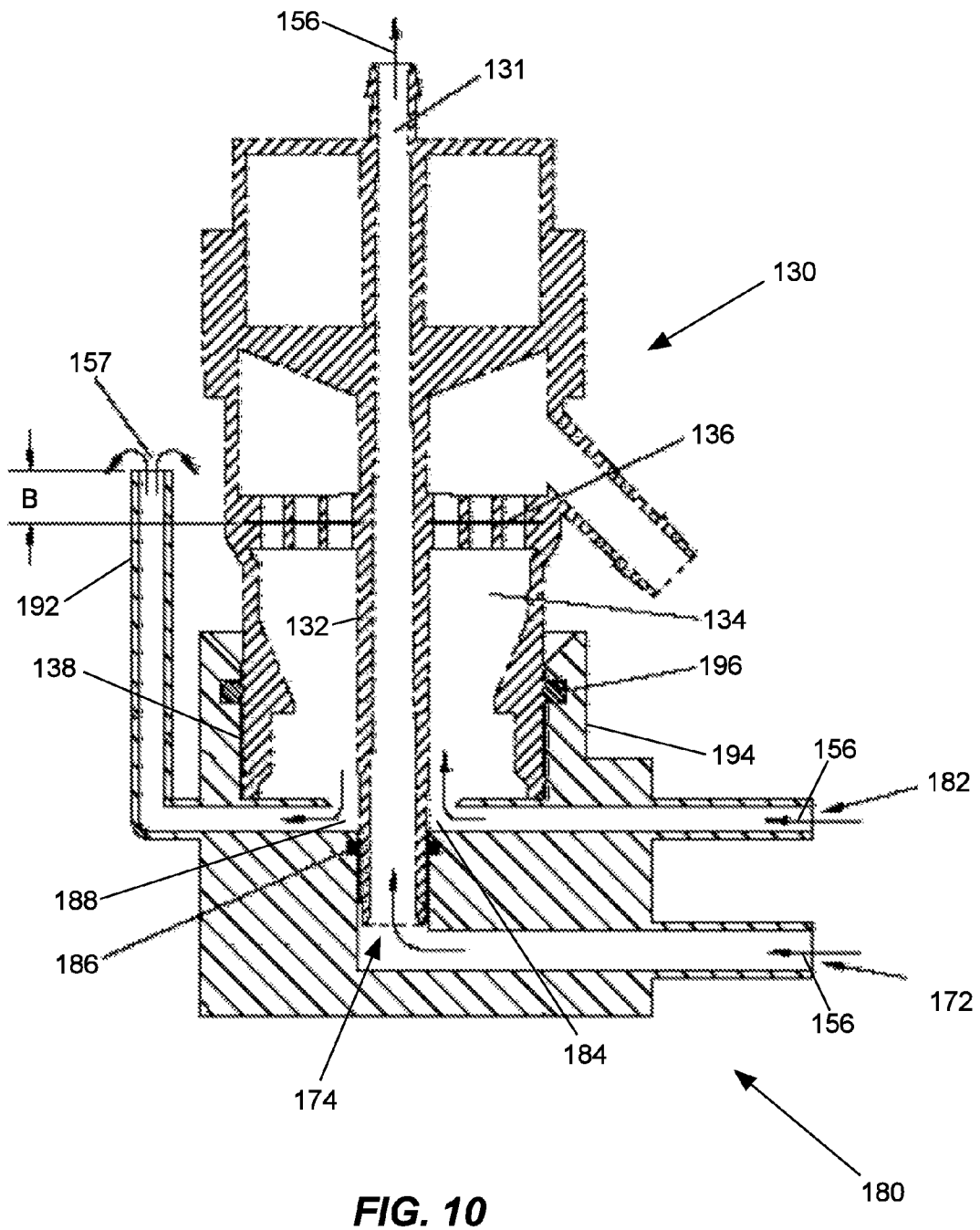
FIG. 10 is a cross-sectional side view of the separator and separator receptacle, in accordance with another representative embodiment.

Illustrated in FIG. 10 is another representative embodiment of the separator receptacle 180 in which the collection chamber 134 can be cleaned in a bath 190 of cleaning solution. The collection chamber bath 190 can formed when the separator 130

TABLE 1

Sanitizing Solutions & Neutralizing Agents

| Sanitizing Agents by Classes | Possible Concentrations* | Exposure Times* | Neutralizing Agents** |
|---|---|---|---|
| LIQUIDS | | | |
| Gluteraldehyde | 1-5% | 2-120 sec. | Solution containing Sodium Bisulfite |
| Peroxide | 0.5-10% | | Solution containing Catalase |
| Peracetic acid | — | | — |
| Acetic acid | — | | — |
| Chlorine Dioxide | 10-10,000 ppm | | — |
| Chlorine | .01-15% | | Solution containing Sodium Thiosulfate |
| Iodophor | 0.1%-25% | | — |
| Alcohol | 70-100% | | Time or Air flow |
| Phenolic | 0.1-10% | | Polysorbate 80 |
| Quaternary Ammonium Compounds | 0.1-5% | | Solution containing Aryl Sulfonate Complex; Lecithin based solutions |
| Ozonoated liquid | 0.01-3 ppm | | Solution containing organic material |
| Heated Water/liquid | — | | Cool liquid; time |
| GASES | | | |
| Ozone | — | 2-120 sec. | — |
| Chlorine Dioxide | — | | — |
| Heated Air | — | | — | is inserted into the separator receptacle 180 until the outer surface of the collection chamber skirt 138 seals with the retention seal 196. Moreover, a pre-determined volume for the collection chamber bath 190 can be formed when the bottom of the collection chamber skirt 138 comes in contact with the bottom 195 of the rinse chamber 194. The collection chamber 134 can then be filled with cleaning solution 156 entering from collection chamber rinse nozzle 184 to create the collection chamber bath 190. Cleaning solution can fill the bath and flow out of the top opening in a snorkel or overflow tube 192 that is coupled to a rinse chamber outlet 188. The snorkel 192 can create a small amount of hydrostatic pressure in the collection chamber bath 190 to force any remaining air out of the collection chamber 134 through the separator filter 136 until the cleaning solution is in contact with the separator filter 136 and the filter supports. The separator filter 136 can be configured to pass air, but not fluids such as the cleaning solution 156 or the sample solution. The hydrostatic pressure in the collection chamber bath 190 can be established by the flow rate of cleaning solution and the height of the snorkel 192 above the bottom surface of the separator filter 136, or distance "B". Alternatively, a fixed or controllable valve, such as a needle valve, can be used at the rinse chamber outlet 188 to apply the small amount of pressure or "head" to the bath of cleaning solution inside the collection chamber.

Simultaneous with the formation of the collection chamber bath 190, the collection bottle stem 132 can be inserted into the vacuum pathway rinse port 174 centered within the separator receptacle 180 and seal against the stem seal 186, and the vacuum pathway rinse 172 can apply cleaning solution 156 to the inside of the collection bottle stem 132 as it flows up and out through the separator inlet 131. As described in the previous embodiment, the cleaning solution 156 can continue beyond the separator inlet 131, through the vacuum tubing and the sampling head (not shown), and out the vacuum orifice.

Figure 11:
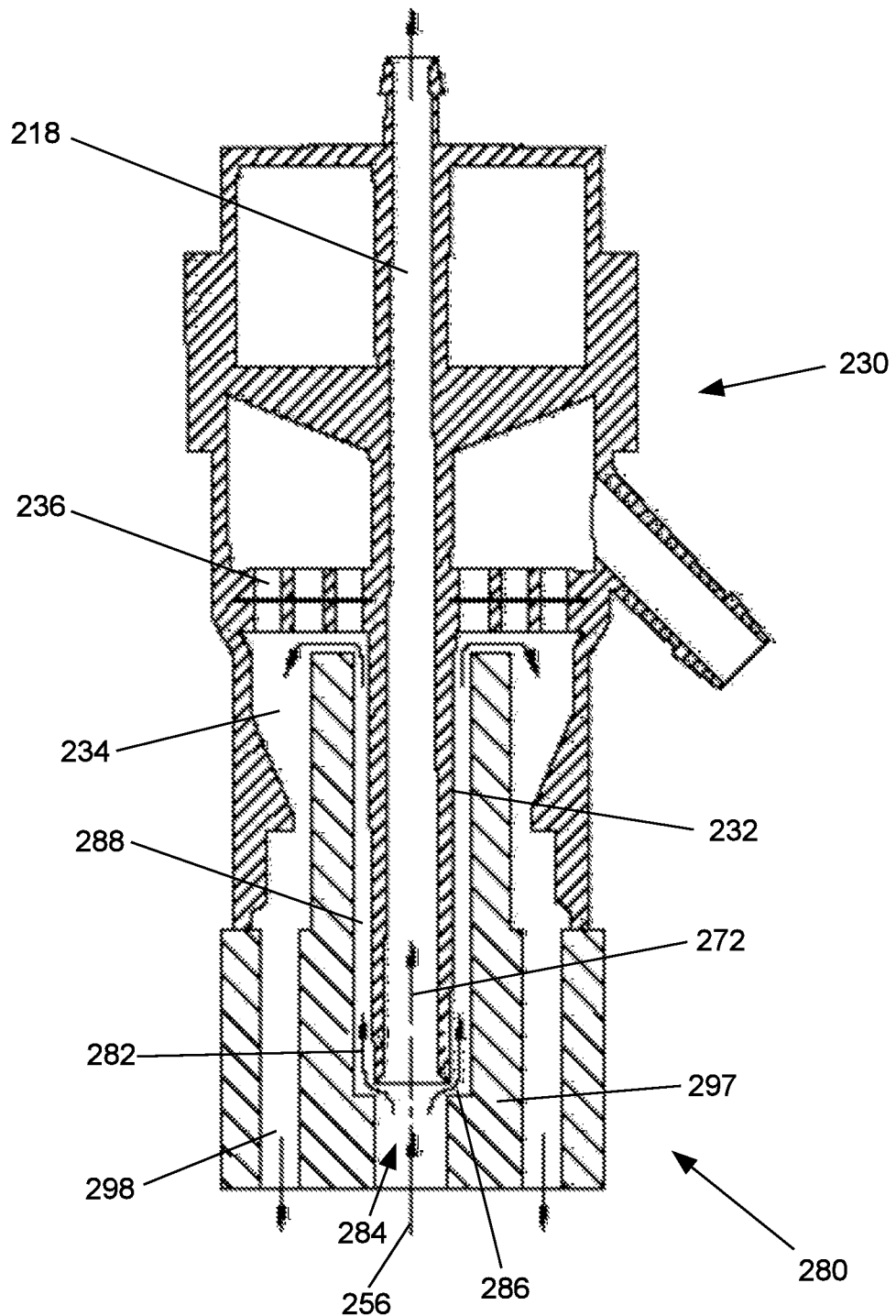
FIG. 11 is a cross-sectional side view of the separator and separator receptacle, in accordance with yet another representative embodiment

Illustrated in FIG. 11 is yet another embodiment of the separator receptacle 280, in which the base 297 of the separator receptacle 280 can be configured with a collection chamber rinse nozzle 284 having a stepped fit 286 which can cooperate with the tip of the collection bottle stem 232 to the separate the cleaning solution 256 into two rinse streams (e.g. the vacuum pathway rinse 272 and the collection chamber rinse 282). The first stream 272 can flow upwards through the inside of the collection bottle stem 232 and into the vacuum pathway 218, while the second stream 282 can flow upwards through an annular chamber 288 surrounding the exterior of the stem 232 to spray against the interior surfaces of the collection chamber 234 and separator filter 236 of the separator 230, before flowing back down through the collection chamber 234 and out through the rinse drains 298 formed into the base 297 of the rinse receptacle 280. In one aspect the stepped fit 286 can be configured so that about 1/10th of the cleaning solution 256 is directed through the vacuum pathway rinse 272 while 9/10th's of the cleaning solution 256 can be directed through the collection chamber rinse 282. However, other proportions for the self-metered rinse streams are also possible.

Alternatively, and an accordance with yet another representative embodiment, the separator receptacle 680 can comprise a loosely-fitting cup or rinse chamber 694 with continuous or intermittently flowing collection chamber rinse 682 for washing the collection chamber as the used cleaning solution 657 overflows into the dipping tank below 664 (see FIG. 16), along with a vacuum pathway rinse 672 for directing the cleaning solution into the vacuum pathway, which includes the inside of collection chamber stem, vacuum tubing and sampling head (not shown), when the separator is inserted into the separator receptacle 680. The level of solution in the cup 694 must be at a level sufficient to fill the collection chamber up to and including all the lower surfaces of the separator filter and filter support.

Referring back to FIGS. 12-13, illustrated therein is another representative embodiment of the wash system 300 in which the cleaning of the vacuum pathway 318 and the collection chamber 334, the separator filter 336, and the outer surfaces of the collection bottle stem 332 can be accomplished in separate stages. As shown in FIG. 12, the vacuum pathway rinse 372 can comprise a post interface 380 which is designed to mate and seal with the collection bottle stem 332 of the separator 330. The sampling head 320 can be held over the dipping tank 364 of the rinse appliance 360 such that the vacuum orifice 322 will drain into the dipping tank 364 as cleaning solution 356 is flowing through the vacuum pathway rinse 372. The cleaning solution 358 in the dipping tank 364 can also be used to clean the exterior of the head end 324 of the sampling head 320, including the region around the vacuum orifice 322. After the vacuum pathway rinse 372 has been completed the separator 330 can be removed from the post interface 380 and dipped into the cleaning solution 358, as shown in FIG. 13. The separator 330 may be tipped back and forth and shuttled side to side until the collection chamber 334, the separator filter 336 and the collection bottle stem 332 have all come in contact with the cleaning solution.

Figure 14:
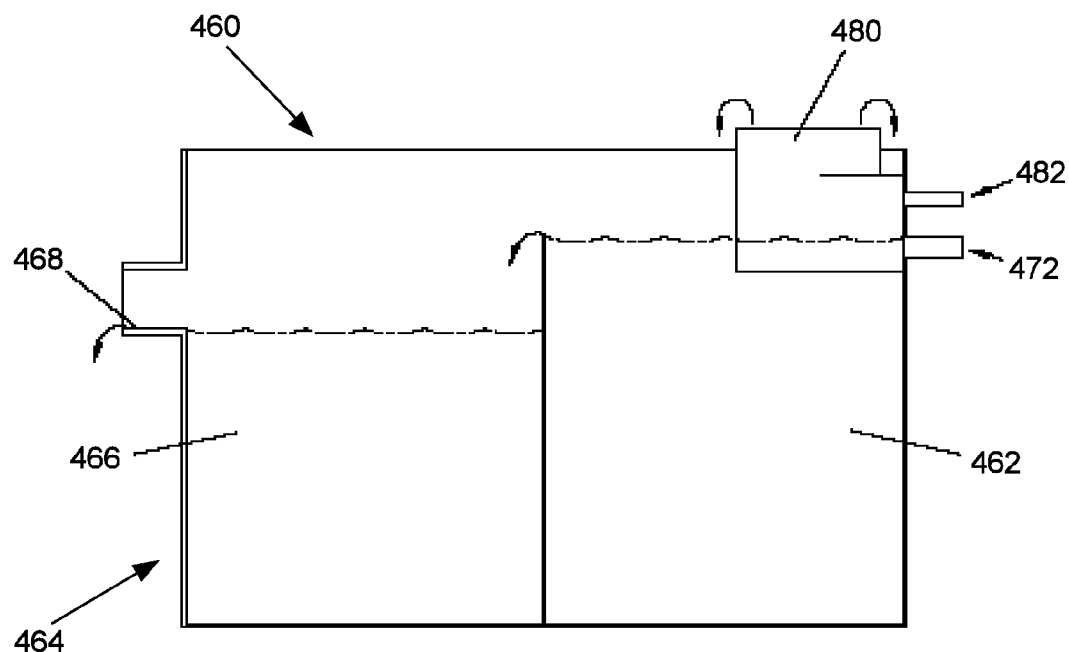
FIG. 14 is a schematic side view of a dipping tank, in accordance with another representative embodiment.

It is possible for the rinse appliance 460 of the wash system to be configured with different levels of cleaning solution cleanliness, as shown in FIG. 14. For example, in one aspect the dipping tank 464 may comprise a series of sub-tanks represented in the drawing as the first tank (or separator receptacle) 480, the second tank 462 and the third tank 466. As described above, the cleaning solution may be fresh as it enters the first tank 462 via the collection chamber bath 482 and the vacuum pathway rinse 472, as described above, or they may be drawn in a clean method from the third tank 466. As the system runs the first tank 480 for cleaning the internal surfaces of the contaminant collection device can be the cleanest of the three tanks. The second tank 462 can be utilized for washing the exterior surface that cannot be done in the first tank 480, but which is better accomplished in cleaning solution that is substantially-free from the floating contaminants or debris that may be found in the cleaning solution of the third tank 466. In one aspect the floating contaminants and debris can be configured to cascade with the cleaning solution from tank to tank until departing out of the third tank 466 via the drain 468. Although three tanks are shown in the representative embodiment of FIG. 14, the principle of creating different levels of cleaning solution cleanliness could be utilized with more or fewer tanks.

As described in FIGS. 3-14 above, the wash system described herein can provide one or more flows of cleaning solution moving in a reverse direction (with respect to normal operation) from the separator, through the vacuum tube and out through the sampling head, and under a positive pressure. It should not be construed, however, that the present invention is limited to the direction of flow or the application of positive pressure as described above. Indeed, the direction of flow of the cleaning solution can be in either direction, and can take place under the application of either positive or negative (e.g. vacuum) pressure.

Figure 15:
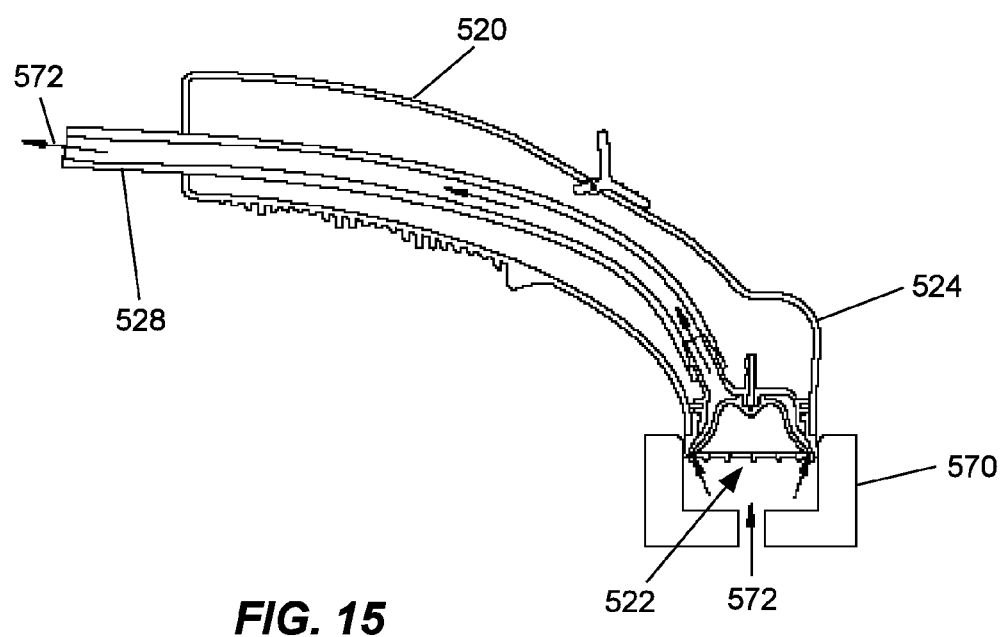
FIG. 15 is a schematic side view of a sampling head and sampling head receptacle, in accordance with another representative embodiment.

For instance, in another representative embodiment of the wash system illustrated in FIG. 15, the direction of flow of the cleaning solution is the same as the direction as the vacuum flow during normal operation (e.g. in from the vacuum orifice in the sampling head, through the vacuum tubing, and out through the separator) and under positive pressure. In this embodiment the head end 524 of the sampling head 520 can be placed inside a rinse receptacle 570 that is connected to a pressurized sourced of cleaning solution, and which can force a vacuum pathway rinse 572 up through the vacuum orifice 522, into the vacuum tubing 528 and out through the separator (not shown), to kill or remove any residual pathogen or bacteria contaminants located on or within the collection equipment. Additionally, as may be appreciated by one of skill in the art, other configurations for applying a cleaning solution to clean a plurality of pathogen or bacteria collection equipment components are possible and can be considered to fall within the scope of the present invention.

Figure 16:
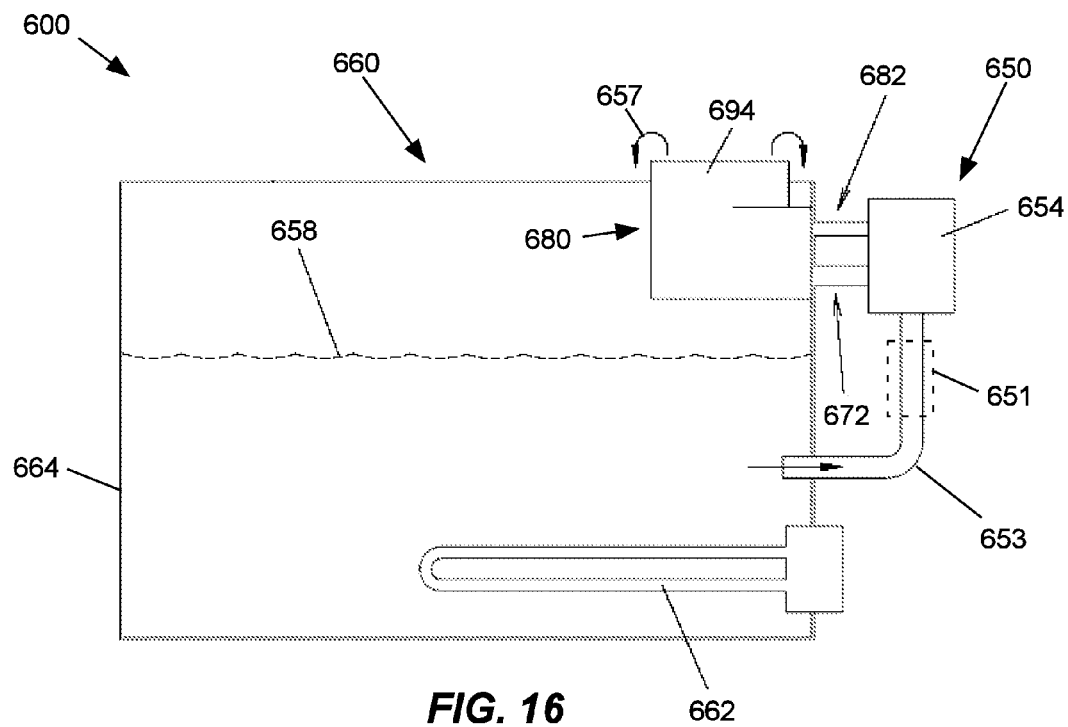
FIG. 16 is a schematic side view of a dipping tank, in accordance with yet another representative embodiment.

FIG. 16 is a schematic side view of the dipping tank 664 of a rinse appliance 660, in accordance with one representative embodiment 600 of a wash system which can be substantially self-contained and portable. Similar to the embodiments described above, the rinse appliance 660 can include a separator receptacle 680 positioned over the dipping tank 664 so that any cleaning solution 657 which drains or overflows from the rinse chamber can be captured with the dipping tank 334. Likewise, a pool of cleaning solution 658 can be maintained inside the dipping tank 664 for use in cleaning the sampling head (not shown), and a recycle line 653 can connect the cleaning solution in dipping tank 664 with the pressurizing unit 654, so as to provide the wash system 600 with a source of pressurized cleaning solution 650. In one aspect either the pressuring unit 654 or the recycle line 653 can include a filtration unit 651 for filtering any contaminant material from the cleaning solution that is received from the dipping tank prior to pressurization and introduction back into the separator receptacle 680 through either a first a vacuum pathway rinse stream 672 or a second collection chamber rinse stream

682. Since the cleaning solution 658 can be continuously recycled through the wash system 600 illustrated in FIG. 16, a water heater 662 with thermostatic control, or a similar cleaning solution conditioner, can be provided within the dipping tank 664 so as to keep the cleaning solution in optimum condition (e.g. for example, at 180 degrees Fahrenheit in the representative hot water example) for the destruction of any pathogens or bacteria coming into contact with the cleaning solution.

Figure 17:
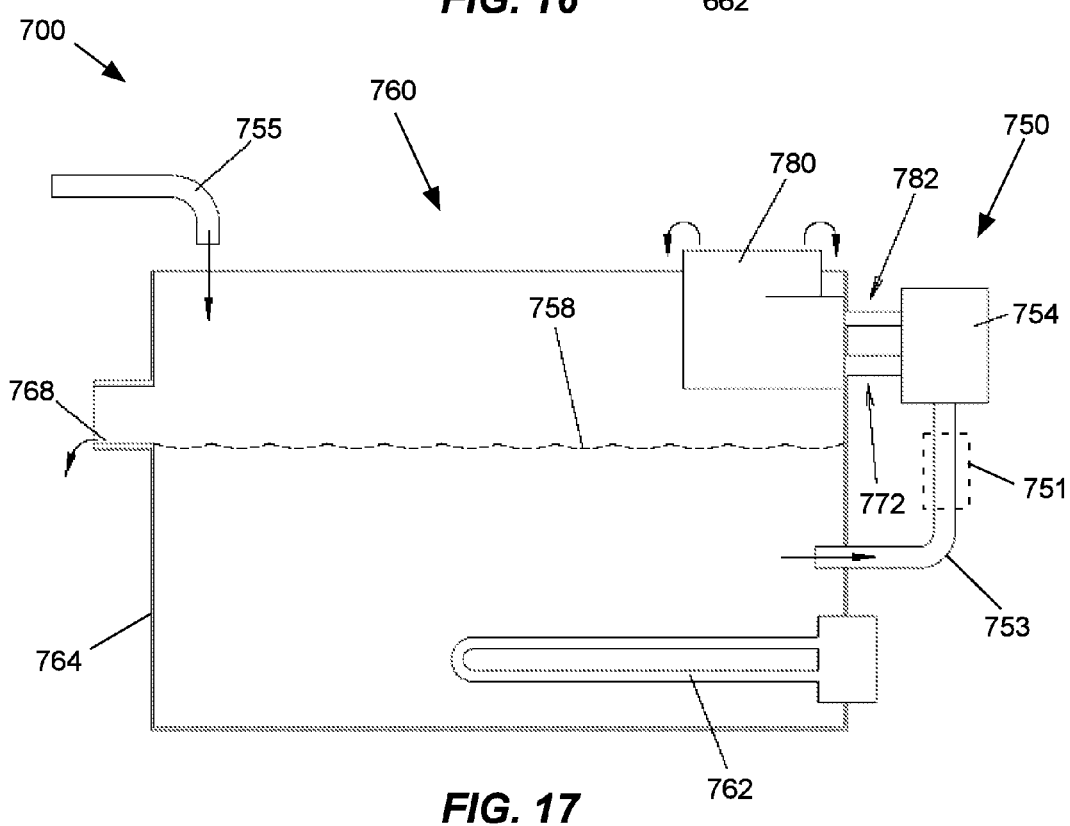
FIG. 17 is a schematic side view of a dipping tank, in accordance with another representative embodiment.

FIG. 17 is a schematic side view of the dipping tank 764 of a rinse appliance 760, in accordance with another representative embodiment 700 of the wash system, and which is similar to recycling wash system described above with reference to FIG. 16 except that a cleaning solution make-up line 755 can be included for providing a continuous or intermittent flow of fresh cleaning solution 756 directly into the dipping tank 764. A drain 768 can also provided for removing the uppermost portion of the cleaning fluid that is likely to contain the floating contaminants or debris that has been washed from the components of the contaminant collection system. The drain 768 can also be used to maintain the pool of cleaning solution 758 already within the dipping tank 764 at a substantially constant level.

Figure 18:
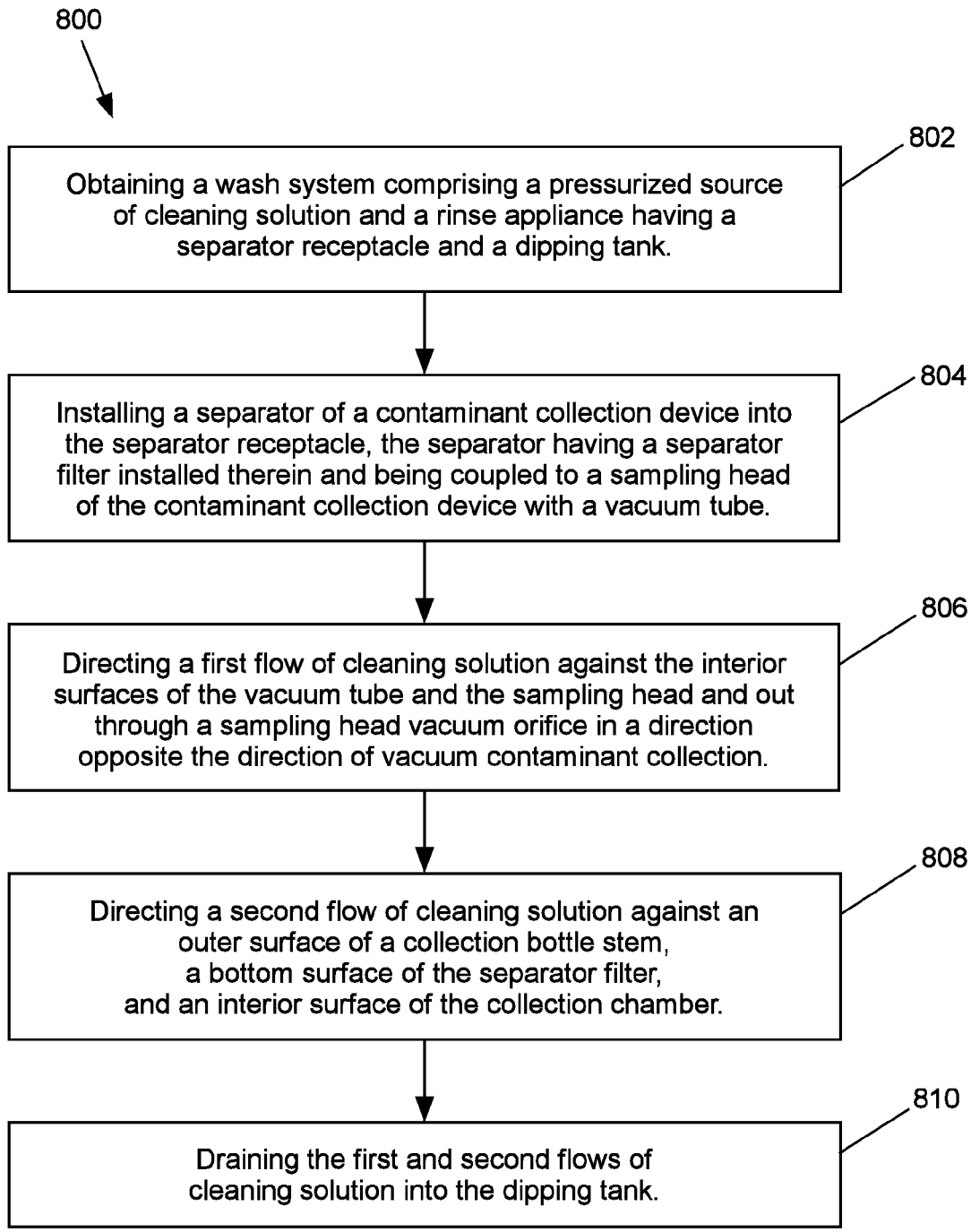
FIG. 18 is a flowchart depicting a method for cleaning the exposed surfaces of a contaminant collection device, in accordance with another representative embodiment.

FIG. 18 is a flowchart depicting a method 800 for cleaning the exposed surfaces of a contaminant collection device, which method includes the steps of obtaining 802 a wash system comprising a pressurized source of cleaning solution and a rinse appliance having a separator receptacle and a dipping tank, and installing 804 a separator of the contaminant collection device into the separator receptacle with the separator being coupled to a sampling head with a vacuum tube. The method also includes the steps of 806 directing a first flow of cleaning solution against a plurality of interior surfaces of the sampling head and the vacuum tube and out through a sampling head vacuum in a direction opposite a direction of vacuum contaminant collection, and directing 808 a second flow of cleaning solution against an outer surface of a collection bottle stem and an interior surface of the separator. The method further includes draining 810 the first and second flows of cleaning solution into the dipping tank.

The foregoing detailed description describes the invention with reference to specific representative embodiments. However, it will be appreciated that various modifications and changes can be made without departing from the scope of the present invention as set forth in the appended claims. The detailed description and accompanying drawings are to be regarded as illustrative, rather than restrictive, and any such modifications or changes are intended to fall within the scope of the present invention as described and set forth herein.

More specifically, while illustrative representative embodiments of the invention have been described herein, the present invention is not limited to these embodiments, but includes any and all embodiments having modifications, omissions, combinations (e.g., of aspects across various embodiments), adaptations and/or alterations as would be appreciated by those skilled in the art based on the foregoing detailed description.

What is claimed is:

1. A wash system for cleaning the exposed surfaces of a contaminant collection device, comprising:
    a source of pressurized cleaning solution; and
    a rinse appliance comprising:
        a first flow path adapted to direct the pressurized cleaning solution against a plurality of interior surfaces of a sampling head of the contaminant collection device and a vacuum tube that couples the sampling head to a collection chamber of the contaminant collection device; and
        a tank adapted to receive the cleaning solution after passing through the first flow path;
    wherein the rinse appliance is adapted to direct cleaning solution into the first flow path and out through a sampling head vacuum orifice in a direction opposite a direction of vacuum contaminant collection.

2. The wash system of claim 1, wherein the rinse appliance includes a sampling head holder for supporting the vacuum orifice above the tank.

3. The wash system of claim 1, further comprising a sampling head receptacle for directing the first flow path of cleaning solution in through a sampling head vacuum orifice in a same direction as a direction of vacuum contaminant collection.

4. The wash system of claim 1, further comprising a second flow path adapted to direct the pressurized cleaning solution against a plurality of interior surfaces of the collection chamber and a separator filter installed therein.

5. The wash system of claim 4, wherein the wash system is adapted to apply the pressurized cleaning solution simultaneously to the first and second flow paths.

6. The wash system of claim 4, wherein the wash system is adapted to provide individually controllable streams of pressurized cleaning solution to the first and second flow paths.

7. The wash system of claim 4, wherein the rinse appliance includes a separator receptacle for receiving a separator of the contaminant collection device comprising:
    a vacuum pathway rinse port centered within the separator receptacle and defining the first flow path, and having a sealing surface located therein for receiving a collection bottle stem of the separator; and
    a rinse chamber surrounding the vacuum pathway rinse port and defining the second flow path, and having a collection chamber rinse nozzle formed therein for directing the cleaning solution against the collection bottle stem and the interior surfaces of the collection chamber and the separator filter.

8. The wash system of claim 7, further comprising at least one drain opening in the rinse chamber and adapted to drain the cleaning solution into the tank.

9. The wash system of claim 7, further comprising an overflow tube in fluid communication with the rinse chamber and having a top opening above a level of a bottom surface of the separator filter.

10. The wash system of claim 7, wherein rinse chamber includes a sealing surface for receiving a collection chamber skirt of the separator therein.

11. The wash system of claim 7, wherein the rinse nozzle is axially aligned with the collection bottle stem.

12. The wash system of claim 7, wherein the second flow path enters the collection chamber rinse nozzle at a location off center from the collection bottle stem to generate a vortex flow.

13. The wash system of claim 4, wherein the rinse appliance includes a separator receptacle for receiving a separator of the contaminant collection device comprising:
    a flow passage centered within the separator receptacle and having a stepped fit formed therein, and
    wherein the stepped fit is adapted to cooperate with a tip of the collection bottle stem to separate a stream of cleaning solution into the first and second flow paths.

14. The wash system of claim 1, wherein the tank includes a debris removal surface having a textured pattern formed therein for removing particulate debris from around a sampling head vacuum orifice.

15. The wash system of claim 14, wherein the tank is configured for sonic agitation of the cleaning solution proximate the debris removal surface.

16. The wash system of claim 1, wherein the tank includes a heater for heating the cleaning solution.

17. The wash system of claim 1, wherein the tank is subdivided into at least two sub-tanks having different levels of cleaning solution cleanliness.

18. The wash system of claim 4, wherein the rinse appliance further comprises a third flow path for applying the pressurized cleaning solution to an interior of a collection bottle that can be removably coupled to the collection chamber.

19. The wash system of claim 18, wherein the rinse appliance further comprises a collection bottle receptacle having a collection bottle rinse chamber and a collection bottle rinse spout directed towards an interior of the collection bottle to define the third flow path.

20. The wash system of claim 1, wherein the cleaning solution further comprises heated water.

21. The wash system of claim 20, wherein the heated water is heated to a temperature ranging from at least about 140 degrees Fahrenheit to about 200 degrees Fahrenheit.

22. The wash system of claim 20, wherein the rinse appliance further comprises an additional flow path adapted to direct the heated water directly into the tank and maintain the cleaning solution in the tank at a substantially constant temperature.

23. A wash system for cleaning the exposed surfaces of a contaminant collection device, comprising:
a source of pressurized cleaning solution;
a rinse appliance comprising a tank, a sampling head receptacle and a separator receptacle, the separator receptacle comprising:
a vacuum pathway rinse port centered within a rinse chamber, and having a first sealing surface located therein; and
the rinse chamber surrounding the vacuum pathway rinse port and having a collection chamber rinse nozzle formed therein;
a sampling head of the contaminant collection device installed in the sampling head receptacle with a sampling head vacuum orifice supported above the tank; and
a separator of the contaminant collection device installed in the separator receptacle with a collection bottle stem sealing against the first sealing surface to establish communication with the vacuum pathway rinse port, and with a collection chamber surrounding the collection chamber rinse nozzle,
wherein activation of a vacuum pathway rinse causes pressurized cleaning solution to flow along a first flow path against a plurality of interior surfaces of the sampling head and a vacuum tube that couples the sampling head to an interior of the collection bottle stem, and
wherein activation of a collection chamber rinse causes pressurized cleaning solution to flow along a second flow path against the collection bottle stem and a plurality of interior surfaces of the collection chamber and a separator filter installed therein.

24. The wash system of claim 23, wherein the rinse appliance further comprises a collection bottle receptacle having a collection bottle rinse chamber and a collection bottle rinse spout formed therein, and wherein activation of a collection bottle rinse causes pressurized cleaning solution to flow along a third flow path against an interior surface of the collection bottle.

* * * * *